United States Patent
Tsujii

(10) Patent No.: US 7,099,431 B2
(45) Date of Patent: Aug. 29, 2006

(54) RADIATION IMAGING APPARATUS

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/825,743

(22) Filed: Apr. 16, 2004

(65) Prior Publication Data

US 2004/0258200 A1     Dec. 23, 2004

(30) Foreign Application Priority Data

Jun. 9, 2003     (JP)     ............................. 2003-163703

(51) Int. Cl.
*H01N 23/00*     (2006.01)
*H05G 1/00*     (2006.01)

(52) U.S. Cl. .............................. 378/20; 378/8; 378/62; 378/208

(58) Field of Classification Search .................... 378/4, 378/19, 20, 39, 55, 98.8, 196, 198, 197, 205, 378/207, 208, 195
See application file for complete search history.

(56) References Cited

U.S. PATENT DOCUMENTS

| | | | | |
|---|---|---|---|---|
| 4,057,745 A | * | 11/1977 | Albert | 378/137 |
| 5,117,445 A | | 5/1992 | Seppi et al. | 378/65 |
| 6,152,598 A | * | 11/2000 | Tomisaki et al. | 378/209 |
| 6,459,760 B1 | * | 10/2002 | D'Ambrosio | 378/43 |
| 6,940,948 B1 | * | 9/2005 | Tretiakov et al. | 378/146 |
| 2001/0019599 A1 | | 9/2001 | Guendel | 378/15 |
| 2002/0154728 A1 | * | 10/2002 | Morita et al. | 378/4 |
| 2002/0191736 A1 | | 12/2002 | Shiota | 378/4 |
| 2003/0007601 A1 | | 1/2003 | Jaffray et al. | 378/65 |
| 2003/0099328 A1 | | 5/2003 | Jensen et al. | 378/198 |

FOREIGN PATENT DOCUMENTS

| | | |
|---|---|---|
| DE | 101 18 183 | 11/2002 |
| EP | 1 163 880 | 12/2001 |
| JP | 10-21372 | 1/1998 |
| JP | 2001-217810 | 8/2000 |
| WO | WO 01/60236 | 8/2001 |

* cited by examiner

*Primary Examiner*—Edward J. Glick
*Assistant Examiner*—Irakli Kiknadze
(74) *Attorney, Agent, or Firm*—Morgan & Finnegan, LLP

(57) ABSTRACT

In an apparatus without a helical movement, a reconstruction error considerably increases as a radiation angle increases. In a prior art embodiment, for example, a one-side value of the radiation angle is 9.5 degrees, and it is predicted that the reconstruction error at its periphery considerably increases. In a radiation imaging apparatus including a radiation generating source for radiating radiation to a subject, a rotating unit for rotating the subject exposed to the radiation from the radiation generating source, and a two-dimensional detector for detecting the radiation, a distance between the radiation generating source and the two-dimensional detector is approximately set to a value equal to or more than 240 cm.

18 Claims, 7 Drawing Sheets

RADIATION IMAGING APPARATUS

BACKGROUND OF THE INVENTION

1. Field of the Invention

The present invention relates to a radiation imaging (radiographic) apparatus for forming a three-dimensional image by using a cone beam from a radiation generating unit, and more particularly, to a radiation imaging apparatus in which a distance between a radiation generating unit and a two-dimensional detector is appropriately selected.

2. Related Background Art

In recent years, development of a two-dimensional detector for radiation imaging (also referred to as an FPD (Flat Panel Detector)) has been advanced to acquire digital data of a large-sized image. Japanese Patent Application Laid-Open No. H09-288184 discloses such an FPD. Particularly, for the purposes of a so-called radiography, an imaging apparatus using a two-dimensional detector with a large light receiving surface of 43 (cm)×43 (cm) has been put into a practical use.

On the other hand, an X-ray CT apparatus is known, in which an X-ray detector detects X-rays passing through a subject exposed to the X-rays, and a transmission image (a so-called scanogram or SCOUT image), a tomographic image or a three-dimensional image of the subject is acquired based on an X-ray detection output (the number of photons of the X-rays) from the detector.

In connection with the X-ray CT apparatus for forming a three-dimensional image, a cone-beam CT apparatus has been developed owing to improvement of developed technique of a two-dimensional detector, and so forth. While an X-ray beam is thinly sliced in a Z-direction (this sliced beam is called a fan beam) in a typical X-ray CT apparatus, an X-ray beam expanding also in the Z-direction (referred to as a cone beam) is used, and the cone beam is detected by the two-dimensional detector in the cone-beam CT (referred to as a CBCT). Compared with the CT using the fan beam, the cone-beam CT has a wider range over which the subject can be imaged by a single scanning rotation. The cone-beam CT has accordingly advantages that the number of rotations can be reduced, and imaging efficiency can be increased. In other words, an increase in the imaging efficiency can be attained by widening a cone angle which is a spread of the cone beam. On the other hand, however, in the event that the cone angle is widened too largely, a reconstruction error is liable to occur in a reconstruction image.

With respect to the cone beam CT, there exists a type in which a scan (collection of projection data) is executed while a pair of an X-ray generating source and a detector are rotated around the subject. Japanese Patent Application Laid-Open No. H10-21372 discloses such a type. However, in a case of cone angle below a predetermined angle, a distance between the two-dimensional detector and the radiation generating source must exceed a predetermined value such that all the light receiving surface of the two-dimensional detector with a large light receiving surface can be irradiated with the radiation from the radiation generating source. Accordingly, in the CBCT of the type in which the scan (collection of projection data) is executed while a pair of the X-ray generating source and the detector are rotated around the subject, it is difficult due to a size of the CBCT apparatus to set the distance between the two-dimensional detector and the radiation generating source such that a large light receiving surface of the two-dimensional detector can be effectively used.

On the other hand, development has been advanced in connection with a practical use of the CBCT of a subject rotating type in which a pair of an X-ray generating source and a detector are fixed, and instead the subject is rotated (without a helical movement). For example, Japanese Patent Application Laid-Open No. 2000-217810 discloses a CBCT of such a type.

Further, there is a background of the X-ray radiography that the distance between the subject and the radiation generating source has been sought in a try-and-error manner in its tradition of about a hundred years. In such a background, one criterion of a good X-ray technologist is an ability of appropriately determining the distance between the subject and the radiation generating source. It is thus important in the radiation imaging apparatus to appropriately determine the distance between the two-dimensional detector and the radiation generating source. Hence, to put into a practical use the CBCT of the subject rotating type in which the subject is rotated, and for which the X-ray technologist has no CT scanning experience, it is considered specially critical to appropriately determine the distance between the two-dimensional detector and the radiation generating source.

Furthermore, in the CBCT disclosed, for example, in the above-referenced Japanese Patent Application Laid-Open No. 2000-217810, a distance between a focal position of an X-ray generating apparatus and an input surface of an X-ray image intensifier is set to 1200 mm, a distance between the focal position of the X-ray generating apparatus and a rotational center of a rotating apparatus, i.e., a rotational radius r of the X-ray generating source, is set to 800 mm, and accordingly a visual field of a transmission X-ray image has a spherical shape with a diameter of about 260 mm (260 mmΦ)in a case of the X-ray image intensifier of a 16-inch type (the size of an image plane in a horizontal direction is 400 mm). A cone angle calculated under those conditions is 9.5 degrees on one side, and totally 19 degrees. It is, however, likely that a reconstruction error of the reconstruction image occurs in a peripheral region of the visual field (mainly a peripheral region of the two-dimensional detector), and no appropriate cone angle has not yet been acquired.

Incidentally, in the CBCT of the helical or spiral type (disclosed in the above-referenced Japanese Patent Application Laid-Open No. 10-21372, for example), its cone angle is set to a relatively small value (from one degree to two degrees), and data of an overall object area is collected using a plurality of rotations. Thus, no study of a range of the cone angle, in which the reconstruction error is liable to occur, has been performed in the CBCT of the spiral type.

In the CBCT of the subject rotating type in which a pair of the X-ray generating source and the detector are fixed, and instead the subject is rotated, however, there exists the problem that the distance between the two-dimensional detector and the radiation generating source is not yet appropriately determined. Further, in the CBCT, the reconstruction error of the reconstruction image is likely to occur, and no appropriate cone angle is established.

As discussed in the foregoing, it is conventionally difficult to appropriately determine the distance between the two-dimensional detector and the radiation generating source, and a variety of measures for solving such a problem have been therefore desired.

SUMMARY OF THE INVENTION

It is an object of the present invention to provide a radiation imaging apparatus which is capable of appropriately setting a distance between a two-dimensional detector and a radiation generating source in a CBCT, and in which a reconstruction error is small.

According to one aspect of the present invention, there is provided a radiation imaging apparatus in which a radiation generating source radiates radiation (radioactive ray) to a subject (a human body, for example), a rotating unit rotates the subject exposed to the radiation beam from the radiation generating source, a two-dimensional detector detects the radiation, a calculating unit calculates a distance between the radiation generating source and the two-dimensional detector, and a radiation generating source moving unit disposes the radiation generating source and the two-dimensional detector such that the distance calculated by the calculating unit can be established.

Other objects, features and advantages of the present invention will be apparent from the following descriptions taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

DESCRIPTION OF THE PREFERRED EMBODIMENTS

Embodiments of the present invention will hereinafter be described in detail with reference to the drawings.

Figure 1A:
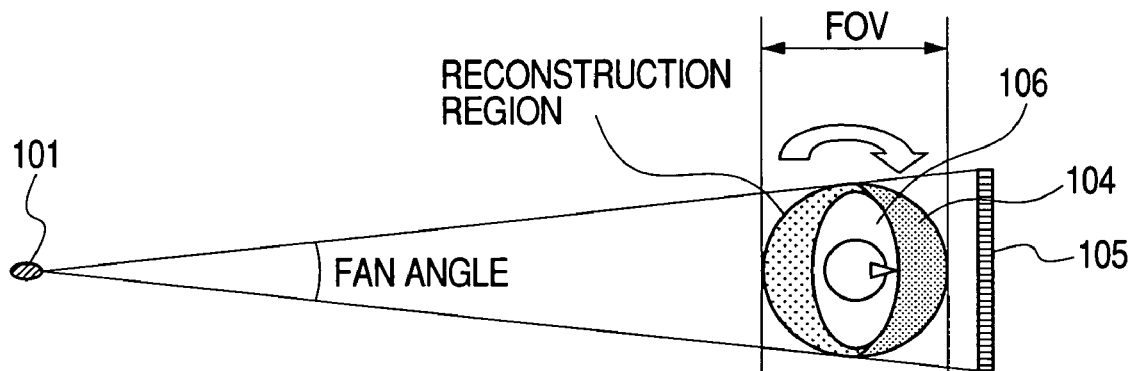
FIG. 1A is a top view illustrating a constructive example of a CBCT of a subject rotating type in which a subject is rotated.
Figure 1B:
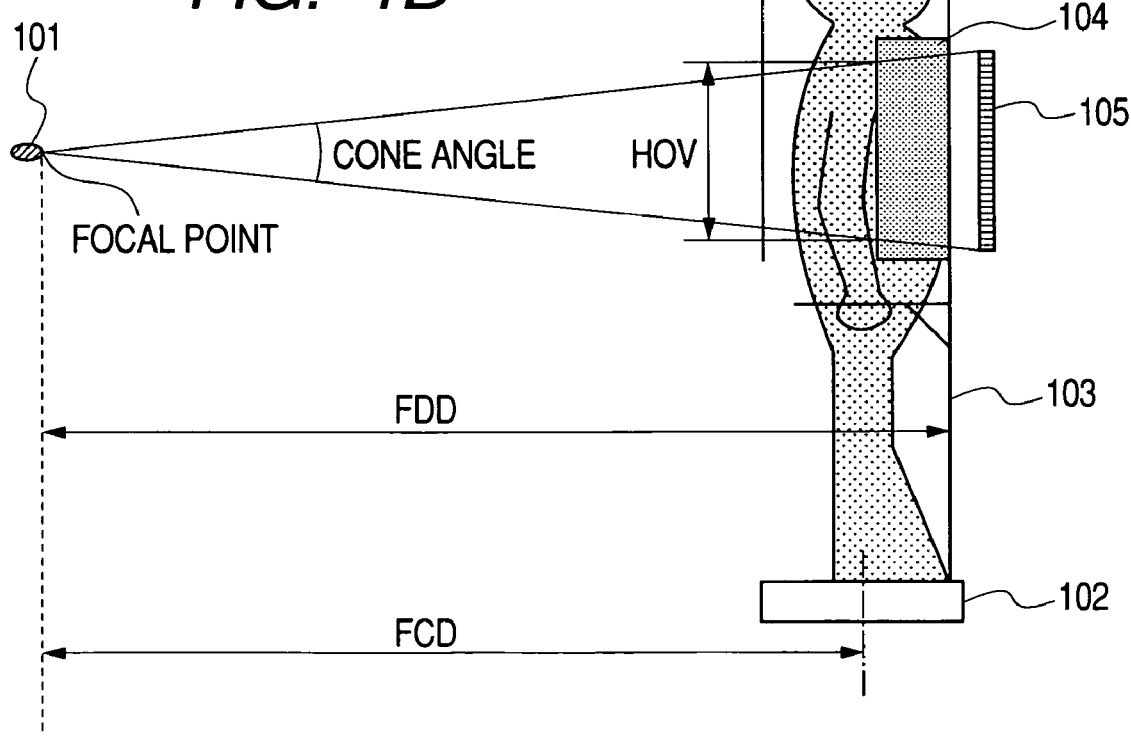
FIG. 1B is a side view illustrating the constructive example of FIG. 1A.

FIGS. 1A and 1B illustrate a constructive example of a CBCT of a subject rotating type in which a subject is rotated. FIG. 1A is a top view thereof, and FIG. 1B is a side view thereof. In FIGS. 1A and 1B, reference numeral 101 designates a radiation generating source for emitting a cone beam of radiation toward the subject, and also designates a focal point of the radiation. As illustrated in FIGS. 1A and 1B, a spread angle of the radiation beam in a vertical direction is called a cone angle, and a spread angle of the radiation beam in a horizontal direction is called a fan angle. Reference numeral 102 designates a rotating table for carrying and rotating a subject 106 to be irradiated with the radiation emitted from the radiation generating source 101. Reference numeral 104 designates a chest plate for fixing the subject 106, which is supported by a supporting pillar fixed to the rotating table 102. Reference numeral 105 designates a two-dimensional detector or sensor. The radiation beam radiated by the radiation generating source 101 passes through the chest plate for fixing the subject, the subject 106, and a grid for removing a scattered beam (not shown), and the transmission beam is detected, and converted into an electrical signal by the two-dimensional detector 105.

Further, the two-dimensional detector 105 is comprised of a semiconductor sensor, for example. In this semiconductor sensor, each pixel has a size of 250 (microns)×250 (microns), and a peripheral size of the sensor has 43 (cm)×43 (cm), for example. In this case, the number of pixels amounts to 1720×1720 (pixels).

In FIGS. 1A and 1B, a distance between the focal point 101 and a rotational center of the rotating table 102 (Focus-Center-Distance) is referred to as an FCD, and a distance between the focal point 101 (also a location of the radiation generating source) and the two-dimensional detector 105 (Focus-Detector-Distance) is referred to as an FDD. A range of a real space, over which a three-dimensional image is to be reconstructed by the CBCT, will hereinafter be referred to as a reconstruction region, and this region is normally a cylindrical region. A height of the reconstruction region is referred to as Height of View, and will hereinafter be abbreviated to HOV. Further, a diameter of the reconstruction region is referred to as an effective diameter of field of view, or Field of View, and will hereinafter be abbreviated to FOV.

Figure 2:
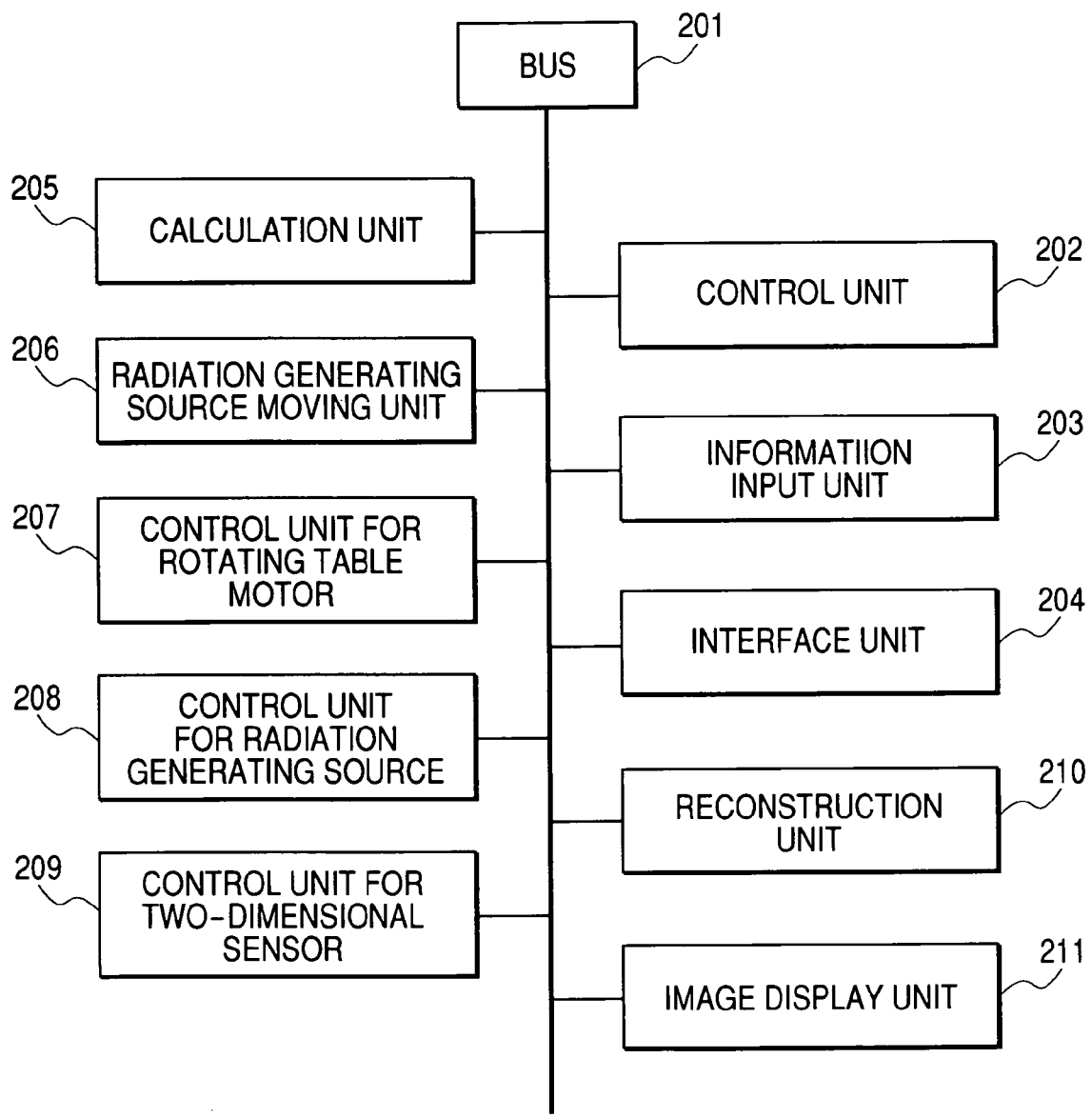
FIG. 2 is a view illustrating a constructive example of a system of the CBCT of the subject rotating type in which the subject is rotated.

FIG. 2 is a block diagram illustrating a structural example of a system of the present invention. In FIG. 2, reference numeral 201 designates a bus through which transmission and reception of control signals and data are executed. Reference numeral 202 designates a control unit for controlling the entire system, which corresponds to a CPU in the case of a computer. Reference numeral 203 designates an information input unit for inputting information of the subject, such as data of a height, a weight, and an area or region to be photographed (a chest area, an abdominal area, a head area, or the like) of the subject. Subject information specific to the imaging area is also input through the information input unit. Particularly, where the chest region is to be imaged, subject information specific to the imaging region, such as a height of a lung field, is also input through the information input unit. Reference numeral 204 designates an interface unit for instructing start of imaging, or giving instructions of system operations such as emergency stop of the system. Reference numeral 205 designates a calculation unit for calculating an appropriate FDD distance between the radiation generating source 101 and the two-dimensional detector 105 based on the subject information input through the information input unit 203, and the like. Reference numeral 206 designates a radiation generating source moving unit for disposing the radiation generating source 101 and the two-dimensional detector 105 by using a moving mechanism including a motor (not shown) such that the distance calculated by the calculation unit 205 can be established between the radiation generating source 101 and the two-dimensional detector 105. In such a disposing operation, either of the radiation generating source 101 and the two-dimensional detector 105 can be moved. The radiation generating source 101 is typically moved, and the radiation generating source moving unit 206 is driven under the control of the control unit 202.

Reference numeral 207 designates a control unit for the rotating table motor for rotating the rotating table 102 under the control of the control unit 202 in response to the instruction of start of CT scanning by the interface unit 204. Reference numeral 208 designates a control unit for the radiation generating source for controlling a radiation state of the radiation generating source 101, such as radiation start and radiation stop, under the control of the control unit 202 in accordance with the instruction, such as the instruction of radiation start, input by the interface unit 204. Reference numeral 210 designates a reconstruction unit for reconstructing a reconstruction voxel(voxel comprises of a plural of section images) from an output image of the two-dimensional detector 105. Reference numeral 211 designates a display unit for displaying the image reconstructed by the reconstruction unit 210, or the distance calculated by the calculation unit 205.

Figure 3:
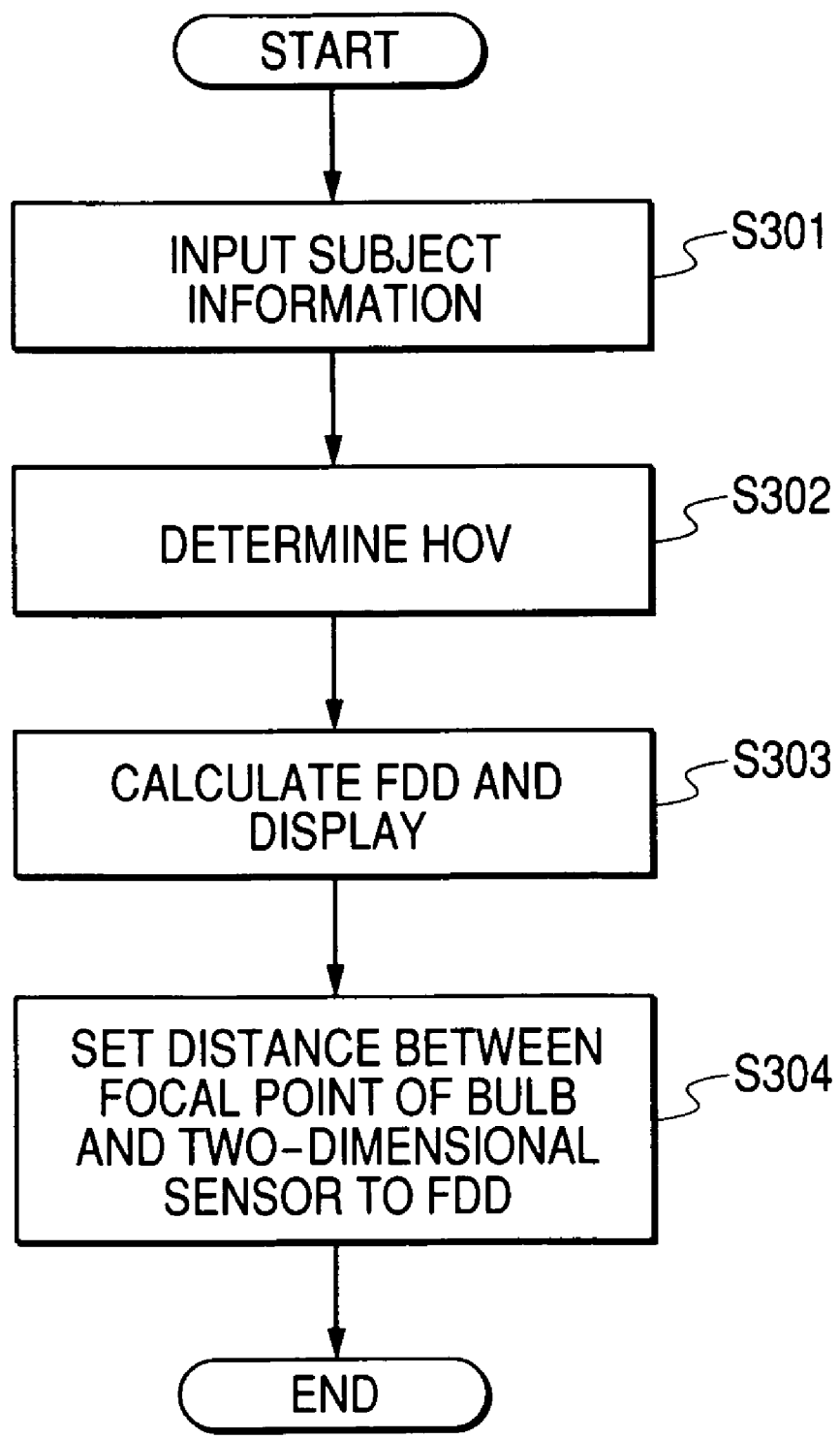
FIG. 3 is a flow chart illustrating a flow of processes for determining an FDD.
Figure 4:
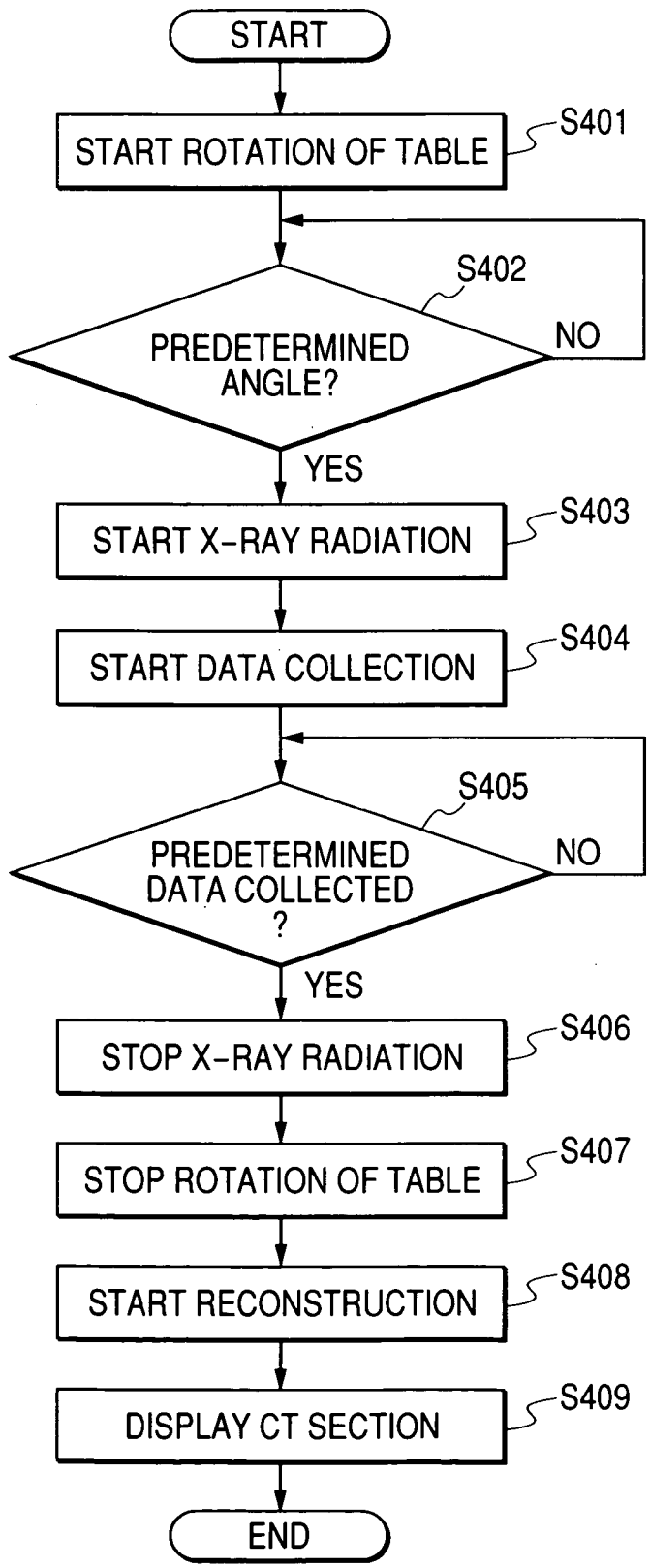
FIG. 4 is a flow chart illustrating a flow of imaging processes in the CBCT.

FIGS. 3 and 4 are flow charts showing flows of processes by the radiation imaging apparatus, respectively. Operation of the CBCT of the subject rotating type in which the subject is rotated will be described with reference to those flows of processes, using CT scanning of a chest area as an example.

In the first place, referring to the flow of FIG. 3, description will be made to a process flow in which the distance of FDD (Focus-Detector-Distance) between the focal point (also the location of the radiation generating source) 101 and the two-dimensional detector 105 is appropriately calculated, and the focal point (also the location of the radiation generating source) 101 and the two-dimensional detector 105 are disposed to establish the calculated FDD therebetween.

An operator, such as an X-ray technologist, inputs patient information, such as a height (body height) and a weight of the subject, through the information input unit 203 prior to start of imaging (CT scanning) (S301). The calculation unit 205 then calculates a height of a lung field (a length of the lung field along a direction of the body height) in a statistical manner from the body height, the weight and the like contained in the patient information. The calculation unit 205 has a conversion table for converting the height and the weight into the height of the lung field, and hence calculates the height of the lung field from the body height and the weight. Generally, a high correlation is recognized between the body height and the height of the lung field. Accordingly, the height of the lung field can be inferred from existing statistical values, and it is possible to infer the height of the lung field more precisely by adding the weight of the patient as the subject information.

In the CT scanning of the chest area, the height of the lung field coincides with the HOV (the height of the reconstruction region) since the lung field is mainly a diagnostic area for a doctor. Therefore, an inferred value of the height of the lung field is determined as a value of the HOV (S302). Particularly, when it is desired to perform a precise CT scanning, it is also possible that the technologist measures the height of the lung field from an appearance of the patient prior to CT scanning, and inputs a measured value. In this case, the measured value itself is the HOV. The reason therefor is that it is desirable that the height of the lung field coincides with the above-mentioned HOV since the lung field is mainly an object of the diagnostic area for the doctor especially in the CT scanning of the chest area.

The calculation unit 205 then calculates the distance between the focal point 101 (also the location of the radiation generating source) and the two-dimensional detector 105 (Focus-Detector-Distance), or the FDD from the determined HOV using the following relation (1) (S303). Here, the calculation unit 205 sets a cone angle $\Phi$ to a value between about six (6) degrees and about ten (10) degrees from the imaging area information input through the information input unit. For an area such as a chest area which has a fine structure, and in which a periphery of the lung field is also an important diagnostic object region, the cone angle $\Phi$ is selected to be less than about ten (10) degrees since a high-resolution image is required overall its reconstruction region. On the other hand, for an area, such as an abdominal area, for which reproducibility of its fine structure is not strictly required, the cone angle may be sometimes selected to be over ten (10) degrees. In this case, the FDD is shorter than a case where the cone angle of ten (10) degrees is selected. Therefore, a radiation dose of the radiation generating source 101 can be oppressed. Although a less error reconstruction image can be obtained as the cone angle is made smaller, the FDD increases in this case, leading to a need of preparing a radiation generating source with a large anodic heat capacity. In contrast, the FDD decreases as the cone angle increases, and the anodic heat capacity of the radiation generating source can be made small. However, as discussed above, the magnitude of the cone angle is naturally limited due to a required resolution of the reconstruction image.

$$FDD=0.5 \times FOV+0.5 \times HOV/\tan(\Phi/2)[mm] \qquad (1)$$

The relation (1) is calculated from the experiment and the clinical test, and the FDD can be preferably set thereby. The relation (1) makes it clear that an appropriate resolution of the reconstruction image can be obtained when the distance between the focal point 101 (also the location of the radiation generating source) and the two-dimensional detector 105 is maintained at a distance over the FDD calculated under a condition that the cone angle $\Phi$ is equal to or less than ten (10) degrees. Detailed description thereof will be made hereinafter. Further, the calculated FDD is simultaneously displayed by the image display unit 211 (S303).

In general, skill is required for the X-ray technologist to determine the distance between the focal point 101 (also the location of the radiation generating source) and the two-dimensional detector 105 (Focus-Detector-Distance) or the FDD. However, since the FDD is calculated by the calculation unit 205 here, the X-ray technologist can readily set the arrangement of the radiation generating source 101 and the two-dimensional detector 105 appropriately. Particularly, the X-ray technologist has no CT scanning experience in the CBCT of the subject rotating type in which the subject is rotated and which will be shortly put into a practical use. It is therefore an important factor for determining the quality of CT scanning to appropriately set the FDD.

The radiation generating source moving unit 206 then disposes the focal point (also the location of the radiation generating source) 101 and the two-dimensional detector 105 such that the distance of the FDD calculated by the calculation unit 205 can be established (S304) Here, the motor (not shown) of the moving mechanism controlled by the control unit 202 is employed, but any general moving mechanism can be used for this purpose. The X-ray technologist can thus automatically obtain the arrangement of the focal point 101 and the two-dimensional detector 105 set at an appropriate distance by performing the input through the information input unit 203. Hence, a precise CT scanning can be speedily executed. Further, a load imposed on the patient and the X-ray technologist can be effectively alleviated.

In the event that no mechanism for automatically operating the radiation generating source moving unit 206 can be provided, the focal point 101 and the two-dimensional detector 105 can be manually disposed by a person based on the FDD calculated by the calculation unit 205 and displayed by the display unit 211. In such a manual arrangement, the FDD is confirmed using a potentiometer. Also in this manual case, the arrangement of the focal point 101 and the two-dimensional detector 105 can be effectively set at an appropriate distance. Hence, a precise CT scanning can be speedily performed. Further, load imposed on the patient and the X-ray technologist can be advantageously alleviated.

Operation during photographing subsequent to completion of the arrangement of the focal point 101 and the two-dimensional detector 105 will be described with reference to the flow chart of FIG. 4.

In response to a signal of start of photographing input through the interface unit 204, the control unit 202 supplies a signal of rotation of the rotating table 102 to the rotating table motor control unit 207 (S401). The control unit 202 monitors an encoder signal (not shown) generated by the rotating table 102 whose rotation is started, and confirms if a predetermined constant speed and an angle of the rotating table 102 have been established (S402). Upon establishment of the predetermined constant speed and the rotation angle of the rotating table 102, the control unit 202 supplies a signal to the radiation generating source control unit 208 to start the X-ray radiation (S403) and start the collection of data (S404). The encoder signal is also employed for determination of integration timing of the data. The rotation of the subject 106 is started when the subject 106 stands on the rotating table 102.

In the event that an encoder which generates 25000 pulses per one rotation of the table is used, data is collected from the two-dimensional detector 105 per 25 pulses of the encoder signal if 1000 views of the projection data are to be collected per one rotation. The control unit 202 counts the encode pulses, and generates an integration signal per 25 pulses, and the dose of X-rays reaching the two-dimensional detector 105 is accordingly counted. The CT scanning is continued until the counted dose reaches a predetermined number (S404 and S405).

In this embodiment, it is assumed that X-rays are continuously generated. However, a generation manner of the X-rays is not limited thereto, and pulses of X-rays can be generated in accordance with the integration segment of the two-dimensional detector 105 based on the encoder signal. Data from the two-dimensional detector 105 is successively transferred to the reconstruction unit 210 through the BUS. The transfer of data is continued until the rotating table 102 has been rotated a predetermined rotational angle, and a predetermined number of views have been collected (S406). When the rotating table 102 has been rotated the predetermined rotational angle, and the predetermined number of views have been collected, the control unit 202 instructs the radiation generating source control unit 208 to stop the X-ray radiation (S406). Thereafter, the rotation of the rotating table 102 is decelerated, and stopped under the control of the control unit 202 (S407).

Immediately after the X-ray radiation is terminated, last projection data is transferred to the reconstruction unit 210. The control unit 202 instructs the reconstruction unit 210 to perform a reconstruction based on the collected projection data (S408). The reconstruction can be started after completion of collection of the entire data. The reconstruction is composed of a pre-process, a filter process, and a process of backprojection. The pre-process consists of an offset process, a LOG conversion, a gain correction, and a defect correction. In the filter process, the Ramachandran function or the Shepp-Logan function is generally used, and it is likewise employed in this embodiment. Data subjected to the filter process then undergoes the backprojection. A Feldkamp algorithm is used as an algorithm from the filter process to the backprojection. When a CT sectional image is reconstructed after completion of the backprojection, the section is displayed by the image display unit 211 (S409). The sectional image is displayed, and the CT scanning is thus completed.

Although the Feldkamp algorithm is used as the reconstruction algorithm in this embodiment, the reconstruction algorithm is not limited thereto. There is a reference paper of "Practical Cone-Beam Algorithm", J. Opt. Soc. Am. A1, 612–619, 1984 by Feldkamp, Davis and Kress.

A geometrical system is shown in the following.

| | |
|---|---|
| Width of two-dimensional detector | 430 mm |
| Height of two-dimensional detector in Z-direction | 430 mm |
| Distance between focal point and rotational center | FCD = 2223 mm (Focus-Center-Distance) |
| Distance between focal point and detector | FDD = 2423 mm (Focus-Detector-Distance) |
| Height of reconstruction | HOV = 350 mm (Height of View) |
| Effective diameter of field of view | FOV = 389 mmΦ (Field of View) |
| Cone angle | Φ = 10 degrees |

As the height of the lung field, a value of about 35 cm is a statistically-high range. In the event that a one-side value of the cone angle is set to five (5) degrees (Φ=10 degrees) based on that statistically-high value, the FCD becomes equal to 2223 mm. At the same time, when the FOV is set to 389 mm, and a value of about 5 mm is secured as a gap between a periphery of the FOV and the sensor, the FDD becomes equal to 2423 mm. When the two-dimensional detector 105 has a square profile, the actual HOV is equal to 389 mm. However, since the one-side value of the cone angle exceeds five (5) degrees in a region beyond 35 cm, an image in this region is considered to be a reconstruction image unsuitable for the diagnosis.

Figure 5:
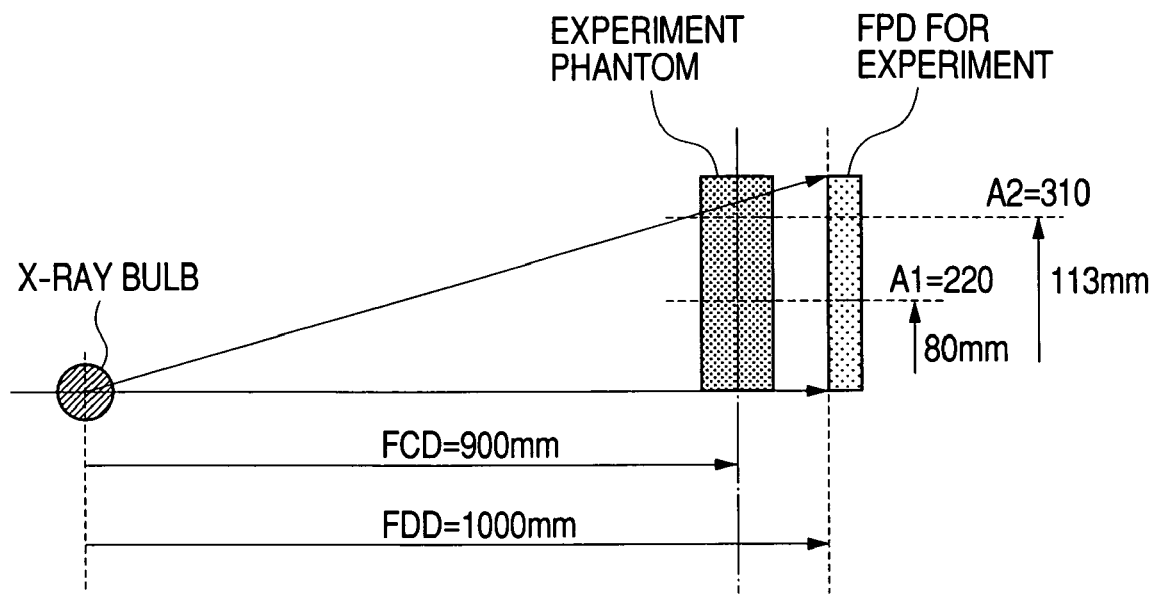
FIG. 5 is a view illustrating an imaging configuration used in an experiment.

As discussed above, the one-side value of the cone angle is preferably equal to or less than five (5) degrees. Experimental data for numerical restriction of this one-side value of five (5) degrees is described below. An experimental CT scanning system is shown in FIG. 5. An experimental phantom placed on the rotating table 102 is disposed at a location at a distance of 900 mm from an X-ray tube. An experimental FPD is fixedly placed at a location at a distance of about 100 mm from a center of the experimental phantom. A resolution of the FPD used for the experiment is 0.64 (mm)×0.64 (mm), and the number of pixels is 384 (a horizontal direction)×224 (a vertical direction).

Figure 6:
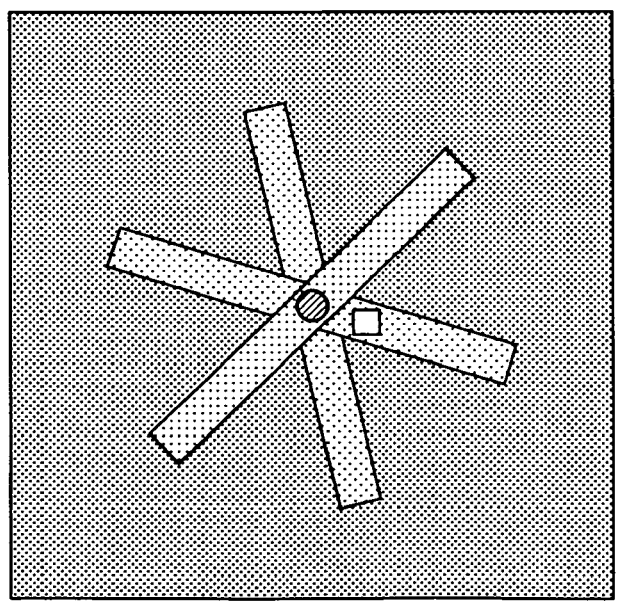
FIG. 6 is a cross-sectional view illustrating an experiment phantom.

A section of the experimental phantom used is illustrated in FIG. 6. The experimental phantom is comprised of an assembly of acrylic plates extending in six (6) directions, and the size in its diametric direction is 100 mm. FIG. 6 illustrates an example of its actual reconstruction image as well. Since the number of reconstruction pixels is 384×384 (pixels), and the diameter of the reconstruction region is 140 mmΦ, the pixel size is 0.365 (mm)×0.365 (mm). The Feldkamp algorithm is used as the reconstruction algorithm. In FIG. 6, a square portion indicated in white is an ROI (Region Of Interest).

Figure 7:
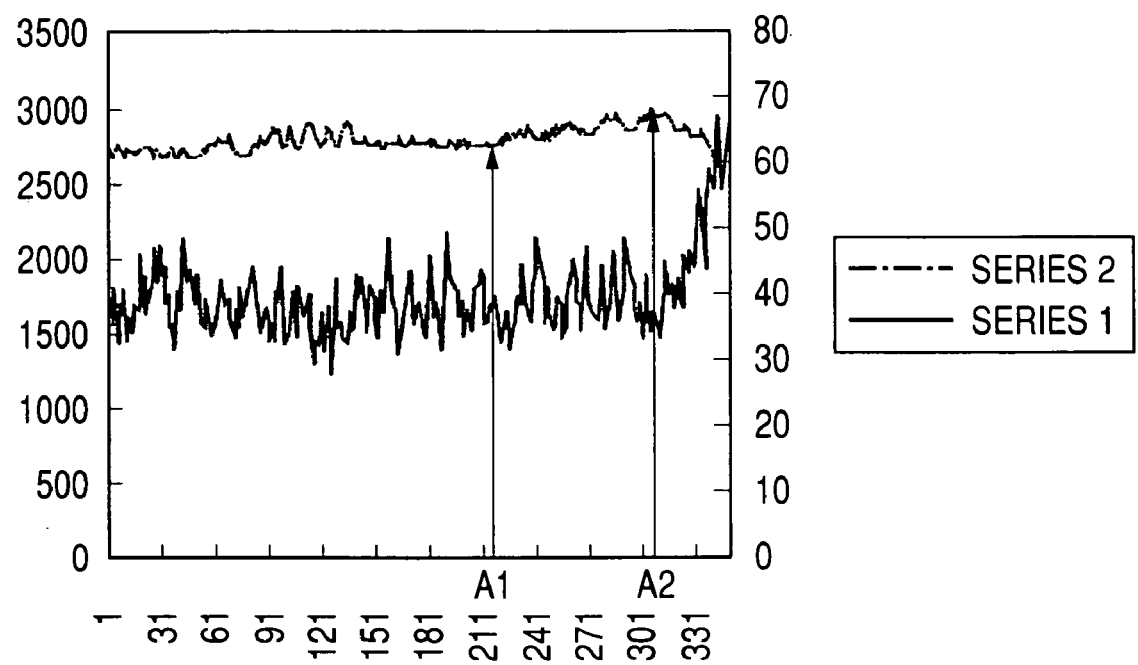
FIG. 7 is a graph showing an average pixel value and a standard deviation of an ROI.

In order to certify limit numerical values of the cone angle, average pixel value and standard deviation of the ROI illustrated in FIG. 6 are employed as indexes. FIG. 7 shows these average pixel value and standard deviation of the ROI in each reconstructed section. Its abscissa represents a number given to the reconstructed section. Sections from 1 to 350 are reconstructed, and a reconstruction pitch of each reconstructed section is 0.365 mm equal to the resolution of the section. In other words, the reconstruction is three-dimensionally carried out with equal resolutions. In FIG. 7, series 1 indicate the average pixel value (a lower waveform), and series 2 indicate the standard deviation (an upper waveform)

As can be understood from FIG. 7, the standard deviation grows bad from a sectional location A1. In FIG. 7, however, bad standard deviations between sections 90 and 120 are due to the sensor artifact, but not to the cone angle. The average pixel value and the standard deviation grow bad from a sectional location A2, which approximately indicates a section at which a line connecting the X-ray tube and the experimental FPD intersects the reconstruction region. In other words, this fact verifies aggravation of the average pixel value and the standard deviation due to shortage of data.

When the cone angle at the sectional location A1 is sought, its one-side value is 5.07 degrees. Namely, the total cone angle is 10.14 degrees.

Figure 8:
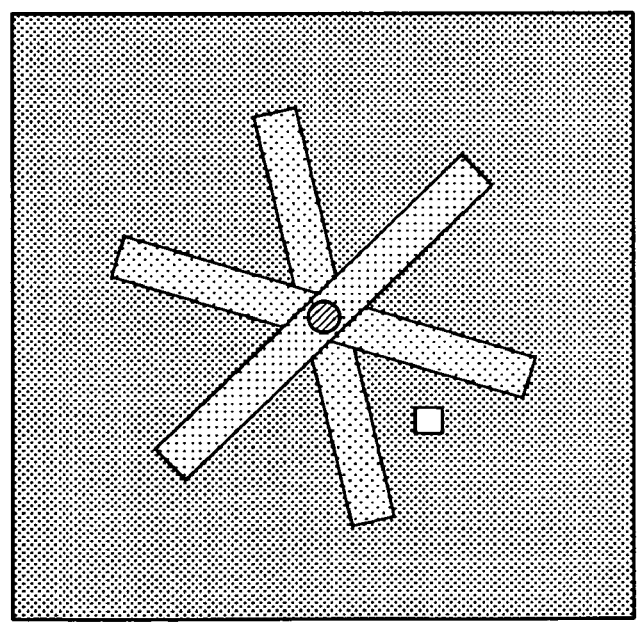
FIG. 8 is another cross-sectional view illustrating the experiment phantom.
Figure 9:
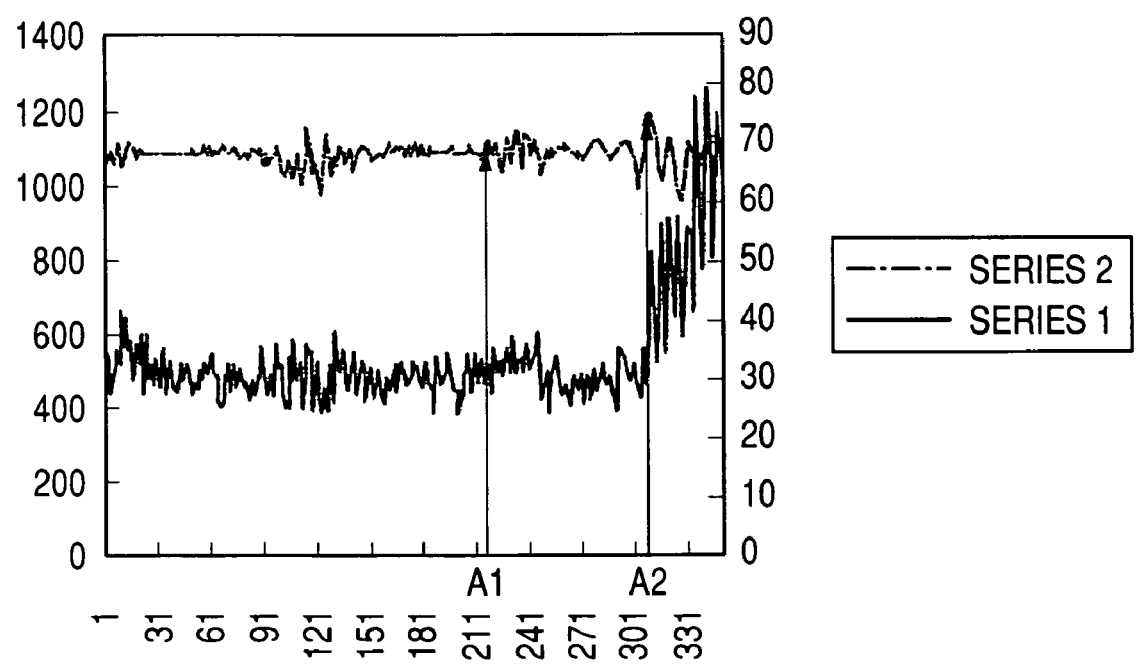
FIG. 9 is another graph showing an average pixel value and a standard deviation of an ROI.

Description will be made to the average value and the standard deviation of a CT value in an air region in the reconstruction image. FIG. 8 illustrates an ROI in the air region, and FIG. 9 shows the average value and the standard deviation in each section. It can be understood therefrom that the air region shows a tendency similar to the acrylic portion. In FIG. 9, bad standard deviations between sections 90 and 120 are due to the sensor artifact, but not to the cone angle, also similarly to the case of the acrylic portion.

The above-discussed experimental results are supported by results obtained when doctors and other persons evaluated images actually acquired at plural cone angles. Thus, the relation (1) is derived from a large number of experimental results and a lot of clinical evaluations. Hence, a preferable FDD can be calculated from the relation (1).

Although an image with a smaller reconstruction error can be acquired as the cone angle is made smaller, the distance between the two-dimensional detector 105 and the radiation generating source 101 must be made longer as the cone angle is made smaller. Accordingly, when the cone angle is decreased, the dose of X-rays to be output from the radiation generating source 101 needs to be increased. It is, however, desirable to dispose the radiation generating source 101 at a place at a distance calculated by the relation (1) in order to oppress the radiation dose of the radiation generating source 101 as much as possible, and obtain a high-quality reconstruction image.

However, in the event that there is a need of acquiring a higher-quality reconstruction image, it is possible to make the FCD and the FDD larger than the above values since a high-output radiation generating source 101 has been developed. Thereby, a preferable reconstruction image with a small reconstruction error can be obtained.

In the radiography, a film with a size of 43 (cm) (a vertical direction)×35 (cm) (a horizontal direction) has been conventionally used. This is because even a person having the largest height of the lung field does not have a height of a lung field exceeding 43 cm. Accordingly, when a value of 430 mm is substituted into the HOV in the relation (1), the FCD becomes approximately equal to 2730 mm. Although the reconstruction region FOV =389 mmΦ in the relation (1), the following relation (2) can be obtained when FOV=500 mmΦ. FOV=500 mmΦ is the common size of CTs of general gantry type CT and the distance between the reconstruction region and the sensor is made equal to 100 mm.

$$FDD = 250 \text{ (mm)} + 100 \text{ (mm)} + 0.5 \times HOV/\tan 5° \quad (2)$$

When HOV=430 (mm) is substituted into the relation (2), the FDD is approximately equal to 3080 mm. Therefore, as a practical range in this radiation imaging apparatus, a preferable range is approximately a range between 2400 mm and 3000 mm.

In the event that the CBCT of the present invention is actually employed, there brings forth a need of executing CT scanning for a large number of subjects in a short time, where a medical examination of the chest area is carried out, for example. In such a case, it is also required that the CT scanning be performed with the FDD being fixed for most of the subjects. As discussed above, considering that most of people generally have heights of the lung field below 35 cm, and that the radiation dose from the radiation generating source must be oppressed as much as possible, it is desirable to set the FDD to about 2400 mm. Accordingly, in the case of imaging the chest area, time for movement of the radiation generating source 101 can be eliminated, leading to improvement of the CT scanning efficiency. Further, the radiation dose from the radiation generating source can be reduced.

Furthermore, considering a rare case of a person whose lung field has a height of about 43 cm, it is also desirable that the FDD is set to a value in a range up to about 3000 mm. Also in this case, time for shifting of the radiation generating source 101 can be eliminated, leading to improvement of the CT scanning efficiency. Further, the radiation dose from the radiation generating source can be reduced. Moreover, this arrangement can also be used for imaging even a subject with a lung field having a height over 35 cm, that is a rare case.

Further, considering a use in a big hospital, there is a need of imaging not only chest areas, but also a large number of abdominal areas, neck areas and the like. Also in such a case, there is a need of setting the FDD to a distance at which all areas can be handled, and an image without reconstruction error can be obtained. In this event, it is desirable to set the FDD to more than 2400 mm, which is also adaptable to the CT scanning of the chest area, as discussed above. In the event that the doctor prefers an image with a smaller reconstruction error, it is desirable to set the FDD to over 2400 mm within a range the output of the radiation generating source permits. Thus, where the FDD is set to a distance equal to or more than 2400 mm, an image with a small reconstruction error can be obtained, and at the same time a large variety of imaging areas can be treated.

As discussed above, a less error reconstruction image can be obtained as the cone angle is made smaller, but a practical range of the cone angle will be discussed from the standpoint of actual employment of the CBCT of this embodiment. In the CBCT of this embodiment, a general radiography (the above-mentioned radiography without any reconstruction) is also considered in the event that the rotation is stopped. Therefore, the apparatus of the present invention needs to support both CT scanning and radiography CT scanning using an X-ray apparatus for general radiography. The X-ray generating apparatus for general radiography can be fabricated at a relatively low cost, as compared with the tube for the X-ray CT, and is widely available in places from clinics to university hospitals.

While the anodic heat capacity of the X-ray tube for use in the X-ray CT is about 7000 KHU, the anodic heat capacity of the tube in the X-ray apparatus for general radiography is in a range between 200 KHU and 300 KHU. The cooling ability per minute of the X-ray apparatus for general radiography is in a range between 15% to 20% of the anodic heat capacity. That value is due to a structure in which radiant heat from the anode and heat conduction from a bearing are received by oil in their vicinities, and the oil is air-cooled by a fan. Here, where the imaging radiation dose of the CBCT in clinics of the chest area is 120 [KV], N [mA] and 5 [sec], the anodic heat capacity (HU) in this CT scanning can be experimentally represented by the following relation in a case of an inverter system $$120 [KV] \times N [mA] \times 5 [sec] \times 1.41 = 846 \times N [HU] \qquad (3)$$

The followings are conditions for chest-area clinical evaluation using the CBCT apparatus of this embodiment.

| | |
|---|---|
| Width of two-dimensional detector | 430 mm |
| Height of two-dimensional detector in Z-direction | 430 mm |
| Distance between focal point and rotational center | FCD = 3067 mm (Focus-Center-Distance) |
| Distance between focal point and detector | FDD = 3417 mm (Focus-Detector-Distance) |
| Effective diameter of field of view (FOV) | FOV = 385 mm |
| Cone angle | Φ = 7.2 degrees |
| X-ray condition | 120 [KV], 100 [mA] |
| X-ray filter | copper 1.5 mm |
| Primary-ray transmission factor of anti-scatter grid | 30% |
| Scanning time of a single rotation | 5 seconds |

The chest-area clinical experiment was carried out for two human bodies under the above conditions, and the image evaluation was performed by the doctor. No disease was discovered, but it was presumed from a degree of discernment of observable blood vessels that a tumorous nodule of 10 mm could be accurately detected. When the apparatus has a detection ability of accurately detecting the tumorous nodule of 10 mm, the apparatus is an effective apparatus for a medical examination and the like.

When the X-ray heat capacity in the case of CT scanning performed under the above conditions is calculated from the relation (3), its value is 84.6 KHU. It is experimentally quite apparent that the image quality of the apparatus according to the present invention can be improved if the dose of X-ray radiation is increased. However, considering the heat capacity of the tube as discussed above, an increase in the dose of X-ray radiation incurs not only an increase in subject's exposure to the radiation, but also an extension of the CT scanning interval. Accordingly, in the event that an image acquired under the above-discussed CT scanning conditions is taken as a reference, a standard image quality can be obtained when the relationship between the X-ray heat capacity, the tube cooling ability C [KHU/min] and the photographing interval T [min] satisfies a relation (4) written as $$C [KHU/min] \times T [min] \geq 84.6 [KHU] \qquad (4)$$

The relation (4) is applied to a system using the general X-ray apparatus. The tube cooling ability C [KHU/min] is C=60 [KHU/min], where the anodic heat capacity is 300 KHU, and the cooling ability is 20%. When the CT scanning interval is two (2) minutes, it is understood that the relation (4) can be satisfied. Here, the shortest one of average intervals between two (2) minutes and three (3) minutes taken at sites of medical examination is adopted. Under those conditions, FDDm≦4069 mm is obtained from the following relation (5) when the maximum FDD (FDDm) is calculated.

$$120 [KHU] \geq 84.6 [KHU] \times (FDDm/3417)^2 \qquad (5)$$

To paraphrase the above, a lower limit (FDDmin) of the FDD and an upper limit (FDDmax) of the FDD can be obtained by the following relations (6) and (7), where the anodic heat capacity is equal to or less than D [KHU], the cooling ability is equal to or less than E [1/min], the CT scanning interval is equal to or less than T [min], the reconstruction height is HOV, and the effective diameter of field of view is FOV.

$$FDDmin = 0.5 \times FOV + 0.5 \times HOV/\tan(\Phi/2) \qquad (6)$$

$$FDDmax = 3417 \times \mathrm{SQRT}(D \times E \times T/84.6) \qquad (7)$$

Here, Φ indicates the cone angle, and its maximum is experimentally 10 degrees. When HOV=350 mm and FOV=389 mm are substituted into the relation (6), FDD=2418 mm can be obtained. It can be understood that the FDD must be approximately set less than four (4) m to achieve the CT scanning interval of two (2) minutes in the CBCT using the general radiography apparatus. When the FDD is set to four (4) m, the cone angle Φ is six (6) degrees.

As described in the foregoing, according to the present invention, the distance between the two-dimensional detector and the radiation generating source can be appropriately set in the CBCT, and a reconstruction image with a small reconstruction error can be obtained.

The present invention is not limited to the above embodiments, and various changes and modifications can be made within the spirit and scope of the present invention. Therefore to apprise the public of the scope of the present invention, the following claims are made.

What is claimed is:

1. A radiation imaging apparatus comprising:
   a radiation generating source for radiating radiation to a subject;
   a rotating unit for rotating the subject exposed to the radiation from the radiation generating source;
   a two-dimensional detector for detecting the radiation; and
   a calculating unit for calculating a distance between the radiation generating source and the two-dimensional detector;
   wherein a cone angle of the radiation from the radiation generating source is selected to be in a range between six degrees and ten degrees based on either of information of the subject and information of imaging conditions, and the calculating unit calculates the distance between the radiation generating source and the two-dimensional detector based on the selected cone angle.

2. An apparatus according to claim 1 wherein there is provided for the calculating unit an input unit for inputting information of the subject, and the calculating unit calculates the distance between the radiation generating source and the two-dimensional detector based on the information of the subject.

3. An apparatus according to claim 1, wherein the calculating unit calculates the distance FDD [mm] between the radiation generating source and the two-dimensional detector based on the following relation $$FDD = 0.5 \times FOV + 0.5 \times HOV/\tan(\Phi/2) \text{ [mm]}$$

where FOV [mm] is an effective diameter of field of view, HOV [mm] is a reconstruction height, and Φ [degree] is the cone angle.

4. An apparatus according to claim 3, wherein there is provided for the calculating unit an input unit for inputting information of the subject, and the calculating unit calculates the HOV based on the information of the subject.

5. An apparatus according to claim 1 further comprising a reconstruction unit for reconstructing an output signal from the two-dimensional detector.

6. A radiation imaging apparatus comprising:
a radiation generating source for radiating radiation to a subject;
a rotating unit for rotating the subject exposed to the radiation from the radiation generating source;
a two-dimensional detector for detecting the radiation; and
a calculating unit for calculating a distance between the radiation generating source and the two-dimensional detector;
wherein the radiation generating source and the two dimensional detector are disposed at locations a distance which is the distance calculated by the calculating unit;
wherein a cone angle of the radiation from the radiation generating source is selected to be in a range between six degrees and ten degrees based on either of information of the subject and information of imaging conditions, and the calculating unit calculates the distance between the radiation generating source and the two-dimensional detector based on the selected cone angle.

7. An apparatus according to claim 6, wherein there is provided for the calculating unit an input unit for inputting information of the subject, and the calculating unit calculates the distance between the radiation generating source and the two-dimensional detector based on the information of the subject.

8. An apparatus according to claim 7, wherein the calculating unit calculates the distance FDD [mm] between the radiation generating source and the two-dimensional detector based on the following relation $FDD=3417 \times SQRT(D \times E \times T/84.6)$ [mm]

where an anodic heat capacity is equal to or less than D [KHU], a cooling ability is equal to or less than E [1/min], and a CT scanning interval is T [min].

9. An apparatus according to claim 2, further comprising a reconstruction unit for reconstructing an output signal from the two-dimensional detector.

10. A radiation imaging apparatus comprising:
a radiation generating source for radiating radiation to a subject;
a rotating unit for rotating the subject exposed to the radiation from the radiation generating source;
a two-dimensional detector for detecting the radiation;
a calculating unit for calculating a distance between the radiation generating source and the two-dimensional detector; and
a radiation generating source moving unit for disposing the radiation generating source and the two-dimensional detector at locations a distance which is the distance calculated by the calculating unit;
wherein a cone angle of the radiation from the radiation generating source is selected to be in a range between six degrees and ten degrees based on either of information of the subject and information of imaging conditions, and the calculating unit calculates the distance between the radiation generating source and the two-dimensional detector based on the selected cone angle.

11. An apparatus according to claim 10, wherein there is provided for the calculating unit an input unit for inputting information of the subject, and the calculating unit calculates the distance between the radiation generating source and the two-dimensional detector based on the information of the subject.

12. An apparatus according to claim 10, wherein the calculating unit calculates the distance FDD [mm] between the radiation generating source and the two-dimensional detector based on the following relation $FDD=3417 \times SQRT(D \times E \times T/84.6)$ [mm]

where an anodic heat capacity is equal to or less than D [KHU], a cooling ability is equal to or less than E [1/min], and a CT scanning interval is T [min].

13. An apparatus according to claim 10, further comprising a reconstruction unit for reconstructing an output signal from the two-dimensional detector.

14. A radiation imaging apparatus comprising:
a radiation generating source for radiating radiation to a subject;
a rotating unit for rotating the subject exposed to the radiation from the radiation generating source; and
a two-dimensional detector for detecting the radiation;
wherein the radiation generating source and the two-dimensional detector are disposed at locations a distance which is in a range between 240 cm and 400 cm, where an imaging height (HOV) is equal to or more than 35 cm, an effective diameter of field of view (FOV) is equal to or more than 39 cm, a tube anodic heat capacity of the radiation generating source is equal to or less than 300 KHU, a tube cooling ability is equal to or less than 20 [1/min], and a radiography interval is equal to or less than two (2) minutes.

15. A radiation imaging apparatus comprising:
a radiation generating source for radiating radiation to a subject;
a rotating unit for rotating the subject exposed to the radiation from the radiation generating source;
a two-dimensional detector for detecting the radiation; and
a calculating unit for calculating a distance between the radiation generating source and the two-dimensional detector;
wherein the calculating unit calculates the distance FDD [mm] between the radiation generating source and the two-dimensional detector based on the following relation $FDD=3417 \times SQRT(D \times E \times T/84.6)$ [mm]

where an anodic heat capacity is equal to or less than D [KHU], a cooling ability is equal to or less than E [1/min], and a CT scanning interval is T [min].

16. An apparatus according to claim 15, wherein there is provided for the calculating unit an input unit for inputting information of imaging conditions, such as an anodic heat capacity, a cooling ability, and a CT scanning interval, and the calculating unit calculates the FDD based on the information of the imaging conditions.

17. A radiation imaging apparatus comprising:
a radiation generating source for radiating radiation to a subject;

a rotating unit for rotating the subject exposed to the radiation from the radiation generating source;

a two-dimensional detector for detecting the radiation; and a calculating unit for calculating a distance between the radiation generating source and the two-dimensional detector;

wherein the radiation generating source and the two dimensional detector are disposed at locations a distance which is the distance calculated by the calculating unit;

wherein the calculating unit calculates the distance FDD [mm] between the radiation generating source and the two-dimensional detector based on the following relation $FDD=3417\times SQRT(D\times B\times T/84.6)$ [mm]

where an anodic heat capacity is equal to or less than D [KHU], a cooling ability is equal to or less than E [1/min], and a CT scanning interval is T [min].

18. A radiation imaging apparatus comprising:

a radiation generating source for radiating radiation to a subject;

a rotating unit for rotating the subject exposed to the radiation from the radiation generating source;

a two-dimensional detector for detecting the radiation;

a calculating unit for calculating a distance between the radiation generating source and the two-dimensional detector; and a radiation generating source moving unit for disposing the radiation generating source and the two-dimensional detector at locations a distance which is the distance calculated by the calculating unit;

wherein the calculating unit calculates the distance FDD [mm] between the radiation generating source and the two-dimensional detector based on the following relation $FDD=3417\times SQRT(D\times E\times T/84.6)$ [mm]

where an anodic heat capacity is equal to or less than D [KHU], a cooling ability is equal to or less than E [l/mim], and a CT scanning interval is T [min].

* * * * *